United States Patent [19]

Stankowiak et al.

[11] Patent Number: 4,898,992
[45] Date of Patent: Feb. 6, 1990

[54] PROCESS FOR THE PREPARATION OF ALKYLENE GLYCOL DIALKYL ETHERS

[75] Inventors: Achim Stankowiak, Burgkirchen; Hildegard Schulz, Triftern, both of Fed. Rep. of Germany

[73] Assignee: Hoechst AG, Frankfurt am Main, Fed. Rep. of Germany

[21] Appl. No.: 302,401

[22] Filed: Jan. 26, 1989

[30] Foreign Application Priority Data

Jan. 30, 1988 [DE] Fed. Rep. of Germany ....... 3802783

[51] Int. Cl.$^4$ ............................................. C07L 41/01
[52] U.S. Cl. ..................................... 568/618; 568/672
[58] Field of Search ........................ 568/618, 692, 625

[56] References Cited

U.S. PATENT DOCUMENTS 4,649,225  3/1987  Bartley .

Primary Examiner—Howard T. Mars

[57] ABSTRACT

In the novel process alkylene glycol monoalkyl ethers of the formula

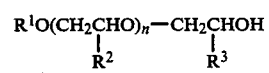

in which $R^1$ is an alkyl radical having 1 to 25 carbon atoms, $R^2$ is H, $CH_3$ or $C_2H_5$ and, within the chain of the polyoxyalkylene radical, arranged randomly or in blocks, can also assume all three meanings, $R^3$ is $CH_3$ or $C_2H_5$ and n denotes 1 to 100, are hydrogenated to give the corresponding alkylene glycol dialkyl ethers in the presence of a supported nickel catalyst using hydrogen without pressure.

5 Claims, No Drawings

PROCESS FOR THE PREPARATION OF ALKYLENE GLYCOL DIALKYL ETHERS

DESCRIPTION

The invention relates to a process for the preparation of alkylene glycol dialkyl ethers from alkylene glycol monoalkyl ethers having a secondary hydroxyl group.

The preparation of alkylene glycol dialkyl ethers from the corresponding monoalkyl ethers is in general carried out according to the already long-known Williamson process or a modification thereof. All these processes start from an alkylene glycol monoalkyl ether, of which in general one terminal hydroxyl group, which can be a primary, secondary or tertiary type, is etherified with an alkylating agent. In detail, in this process the alkylene glycol monoalkyl ether employed is first reacted with alkali to give the glycolate compound. The glycolate is then converted into the desired diether using alkyl halide, dialkyl sulfate or another suitable alkylating agent. This already long-known process for the commercial preparation of alkylene glycol dialkyl ethers from alkylene glycol monoalkyl ethers having a primary, secondary or tertiary hydroxyl group also has further disadvantages in addition to the number of steps. Thus, high amounts of alkali metal halides which can only be utilized with difficulty are produced.

It is also already known to convert compounds having one or more primary, secondary or tertiary hydroxyl groups into the corresponding compounds which are free of hydroxyl groups or into those compounds which contain fewer hydroxyl groups than the starting compounds by catalytic hydrogenation. These hydrogenations are carried out, as a rule, using hydrogen under a more or less high pressure and using Raney nickel, cobalt, copper, chromium, molybdenum, palladium, platinum, ruthenium and the like as catalyst.

Thus, for example, in U.S. Pat. No. 4,649,225, the hydrogenation of alkylene glycols, such as diethylene glycol or triethylene glycol, to give the corresponding ethylene glycol monomethyl and/or ethylene glycol monoethyl ethers is described using iridium as a catalyst. The alkylene glycols containing primary hydroxyl groups employed are cleaved at the terminal carbon-carbon bond or on the terminal carbon-oxygen bond, in the first case the monomethyl ether and in the second case the monoethyl ether, in addition to monoethylene glycol and ethanol as by-products, being formed.

It has now surprisingly been found that certain secondary hydroxyl groups can be hydrogenated with hydrogen at atmospheric pressure using supported nickel catalysts and during this process essentially only the desired compounds are formed. Accordingly, a process has been found for the preparation of alkylene glycol dialkyl ethers from alkylene glycol monoalkyl ethers having a secondary hydroxyl group which comprises reacting an alkylene glycol monoalkyl ether of the formula I

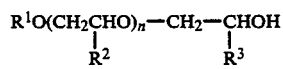

in which $R^1$ is an alkyl radical having 1 to 25 carbon atoms, $R^2$ is H, $CH_3$ or $C_2H_5$ and, within the chain of the polyoxyalkylene radical, arranged randomly or in blocks, can also assume all three meanings, $R^3$ is $CH_3$ or $C_2H_5$ and n denotes 1 to 100, with hydrogen without pressure in the presence of nickel on a support as catalyst and recovering the alkylene glycol dialkyl ether formed from the reaction product.

In the process according to the invention, specific alkylene glycol monoalkyl ethers are therefore hydrogenated to give the corresponding diethers, in particular those monoethers of which one terminal hydroxyl group is a secondary hydroxyl group on an isopropyl radical or on a secondary butyl radical. These hydroxyalkyl radicals which are located at the end of the alkylene glycol chain are hydrogenated to the n-propyl radical ($C_3H_7$) and the n-butyl radical ($C_4H_9$). The diethers obtained using the process according to the invention thus correspond to the formulae below.

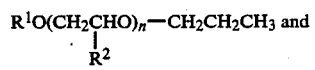

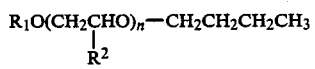

in which $R^1, R^2$ and n have the meanings indicated.

Since the known hydrogenations of primary, secondary or tertiary hydroxyl groups are carried out, as a rule, under pressure and in the case of the use of nickel as catalyst with Raney nickel, it is an unexpected result that the hydrogenation of the alkylene glycol monoalkyl ether in question is only effected without pressure and using a supported nickel catalyst.

The alkylene glycol monoalkyl ethers to be employed in the process according to the invention are known and commercially available. Preferred monoethers are those of formula I in which $R^1$ is an alkyl radical having 4 to 18 carbon atoms, $R^2$ is H or $CH_3$ and—as already mentioned above—within the chain of the polyoxyalkylene radical, arranged randomly or in blocks, can also assume both meanings, $R^3$ is $CH_3$ and n is 5 to 50. The index n can be an integer or a non-integer. The alkylene glycol monoethers to be employed are, as is known, obtained by oxalkylation of the alcohols corresponding to the radical $R^1O$. If the alcohol is reacted with ethylene oxide alone or with ethylene oxide as the last oxalkylation agent, then, as arises from formula I, at least one other propylene oxide unit or butylene oxide unit must also be attached, in order to form an alkylene glycol monoalkyl ether having the secondary hydroxyl group in question; this is precisely the decisive feature of the starting monoether according to the invention. The alcohols employed for the oxalkylation can, according to the meanings of $R^1$, be individual alcohols or alcohol mixtures preferably having 4 to 18 carbon atoms. When using alcohols having a relatively high number of carbon atoms, the available commercial products, such as coconut fatty alcohol, tallow fatty alcohol and the like are preferred (in these fatty alcohols, as is known, alkyl radicals essentially having 8 to 18 carbon atoms are present; the presence of alkenyl groups in these fatty alcohols has no influence on the hydrogenation according to the invention).

The hydrogenation of the alkylene glycol monoalkyl ethers to be employed according to the invention is carried out with the aid of a supported nickel catalyst. Such nickel catalysts are known and commercially available. They consist in general of 5 to 80% by weight of nickel, expediently 30 to 65% by weight of nickel, on a support material, percent by weight being relative to the total catalyst. The support material is not critical. Suitable inert support materials are aluminas, charcoal, kieselguhr, silica, silicon carbide, zeolites, metal oxides and the like. They are characterized by the specific surface area, the pore volume and the mean pore diameter. The support materials are employed, as a rule, in the form of powders, granules, spheres or rings. The catalyst amount to be employed can vary within wide limits. With less than 0.5% by weight of nickel, relative to the alkylene glycol monoalkyl ether, the hydrogenation only proceeds very slowly and larger amounts of nickel than 15% by weight are in general no longer economical. As a rule, the amount of supported nickel catalyst employed is therefore such that 0.5 to 15% by weight of nickel, preferably 1 to 10% by weight of nickel, relative to the amount of alkylene glycol monoalkyl ether to be hydrogenated, is present.

The reaction according to the invention of the alkylene glycol monoalkyl ether indicated with hydrogen is carried out at atmospheric pressure, i.e. without hydrogen overpressure. The reaction can be carried out continuously or batchwise. According to a preferred procedure, the glycol monoether to be hydrogenated and the supported nickel catalyst, preferably in powder form, are initially introduced into a reaction vessel having a reflux condenser. The mixture is heated to the reaction temperature and brought into contact at this temperature, expediently with stirring, with excess hydrogen (the stoichiometric amount of hydrogen is 1 mole per mole of glycol monoether) without pressure. This is preferably carried out in such a way that the hydrogen is passed through the mixture kept at the reaction temperature and the excess hydrogen is removed through the reflux condenser, in the water separator of which the reaction water collects. Although the ratio of amounts of glycol monoether to hydrogen can vary within wide limits, 30 to 500 liters of hydrogen per kilogram of glycol monoether per hour, preferably 50 to 250 liters of hydrogen per kilogram of glycol monoether per hour, are in general employed. With less than the 30 liters of hydrogen mentioned, very long reaction times are required even at a higher reaction temperature and relatively large amounts of catalyst and more hydrogen than the 500 liters mentioned is no longer economical. The reaction temperature is 150° to 300° C., preferably 180° to 250° C. The reaction time until attainment of a practically complete hydrogenation of the alkylene glycol monoalkyl ether to the diether is in the range from 5 to 20 hours. The hydrogenation is expediently monitored by continuous determination of the hydroxyl number of the reaction product. The hydrogenation is complete after attainment of the desired low hydroxyl number in comparison to the high hydroxyl number of the glycol monoether employed. The desired glycol diether is present in the liquid, more or less viscous reaction product. To obtain pure glycol diether, the reaction product is freed from catalyst, any unconverted glycol monoether and any by-products formed. Thus, the supported nickel catalyst can be separated from the liquid reaction products simply by filtration. The alkylene glycol dialkyl ethers obtained using the process according to the invention are, as is known, colorless, more or less viscous liquids. They are obtained in high yields. Only very small amount of by-products are present, if at all.

The invention is now illustrated in more detail by examples. In the comparison examples it is shown that the hydrogenation of the glycol monoether indicated proceeds unsuccessfully to the corresponding diethers if it is not carried out using a supported nickel catalyst but, for example, using Raney nickel, a supported cobalt catalyst, supported palladium catalyst or a supported platinum catalyst, and if it is not carried out without pressure, but under a more or less high hydrogen pressure.

EXAMPLE 1

This example and all other examples were carried out in a reaction vessel which was equipped with a stirrer, thermometer, gas inlet tube and reflux condenser with water separator.

500 g of propylene glycol monobutyl ether of the formula

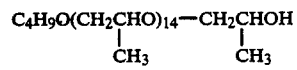

and 39 g of a pulverulent supported nickel catalyst, containing 64% by weight of nickel on alumina/silica as support material, i.e. 25 g or 5% by weight of nickel, relative to the 500 g of monobutyl ether, are initially introduced (the number 14 in the above formula standing for n of the general formula I is, as is known, a mean value). After flushing the reaction vessel with nitrogen, the initially introduced mixture was heated to the reaction temperature of 220° C. with stirring. The hydrogen for hydrogenation was added via the abovementioned inlet tube which dipped into the reaction mixture and the excess was removed via the reflux condenser with water separator. 130 liters of hydrogen per kilogram of glycol monoether per hour were passed through the mixture. As soon as the reaction product exhibited a hydroxyl number of 2 (the glycol monoether employed had the hydroxyl number 80), the hydrogen addition was ended and the reaction product was cooled, nitrogen for flushing being added during the cooling instead of hydrogen. The reaction product which was separated from catalyst by filtration and which mainly consisted of the desired propylene glycol butyl propyl ether was a clear, colorless, viscous liquid. A yield of glycol diether of 97% by weight was calculated from the hydroxyl numbers indicated.

EXAMPLE 2

Batch: 500 g of propylene glycol monobutyl ether of the formula

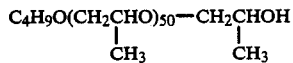

and 23 g of the supported nickel catalyst from Example 1, i.e. 15 g or 3% by weight of nickel, relative to the 500 g of monobutyl ether.

Procedure: Reaction temperature 240° C. Amount of hydrogen 130 liters per kilogram of glycol monoether per hour until the reaction product had a hydroxyl number of 2 (the monoether employed had the hydroxyl number 32). The desired propylene glycol butyl propyl ether was obtained in a yield of 94% by weight.

EXAMPLE 3

Batch: 500 g of propylene glycol monoisotridecyl ether of the formula

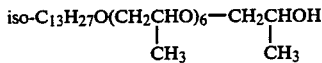

and 77 g of a pulverulent supported nickel catalyst, containing 65% by weight of nickel on kieselguhr as support material, i.e. 50 g or 10% by weight of nickel, relative to the 500 g of monoisotridecyl ether.

Procedure: Reaction temperature 190° C. Amount of hydrogen 50 liters per kilogram of glycol monoether per hour until the reaction product had a hydroxyl number of 1 (the monoether employed had the hydroxyl number 89). The propylene glycol isotridecyl propyl ether was obtained in a yield of 99% by weight.

EXAMPLE 4

Batch: 500 g of propylene glycol monoisotridecyl ether of the formula

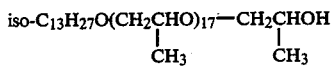

and 62 g of the supported nickel catalyst from Example 3, i.e. 40 g or 8% by weight of nickel, relative to the 500 g of monoisotridecyl ether.

Procedure: Reaction temperature 230° C. Amount of hydrogen 130 liters per kilogram of glycol monoether per hour until the reaction product had a hydroxyl number of 3 (the monoether employed had the hydroxyl number 43). The propylene glycol isotridecyl propyl ether was obtained in a yield of 93% by weight.

EXAMPLE 5

Batch: 500 g of ethylene glycol monoisotridecyl ether of the formula

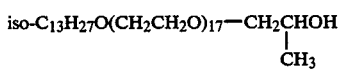

and supported nickel catalyst as in Example 4.

Procedure: As in Example 4. The ethylene glycol isotridecyl propyl ether was obtained in a yield of 95% by weight.

EXAMPLE 6

Batch: 500 g of ethylene/propylene glycol monomethyl ether of the formula

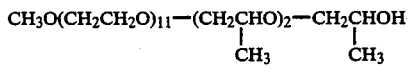

and 56 g of a pulverulent supported nickel catalyst, containing 45% by weight of nickel on kieselguhr as support material, i.e. 25 g or 5% by weight of nickel, relative to the 500 g of monomethyl ether.

Procedure: Reaction temperature 230° C. Amount of hydrogen 130 liters per kilogram of glycol monoether per hour until the reaction product had a hydroxyl number of 11 (the monoether employed had the hydroxyl number 100). The glycol methyl propyl ether was obtained in a yield of 90% by weight.

EXAMPLE 7

Batch: 500 g of tetraethylene/isobutylene glycol monomethyl ether of the formula

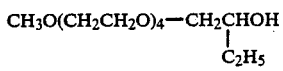

and 110 g of the supported nickel catalyst from Example 6, i.e. 50 g or 10% by weight of nickel, relative to the 500 g of monomethyl ether.

Procedure: Reaction temperature 175° C. Amount of hydrogen 250 liters per kilogram of glycol monoether per hour until the reaction product had a hydroxyl number of 25 (the monoether employed had the hydroxyl number 204). The tetraethylene glycol methyl butyl ether was obtained in a yield of 88% by weight.

EXAMPLE 8

Batch: 500 g of ethylene glycol monococonut alkyl ether of the formula

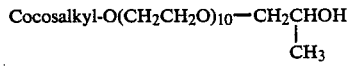

and supported nickel catalyst as in Example 1.

Procedure: Reaction temperature 220° C. Amount of hydrogen 180 liters per kilogram of glycol monoether per hour until the reaction product had a hydroxyl number of 15 (the monoether employed had a hydroxyl number of 82). The ethylene glycol coconut alkyl propyl ether was obtained in a yield of 82% by weight.

EXAMPLE 9

Batch: 500 g of ethylene/isobutylene glycol monococonut alkyl ether of the formula

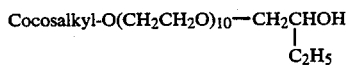

and supported nickel catalyst as in Example 2.

Procedure: Reaction temperature 220° C. Amount of hydrogen 200 liters per kilogram of glycol monoether per hour until the reaction product had a hydroxyl number of 15 (the monoether employed had a hydroxyl number of 80). The ethylene glycol coconut alkyl butyl ether was obtained in a yield of 81% by weight.

COMPARISON EXAMPLES 1 TO 4

Example 1 was repeated four times, Raney nickel and a corresponding supported cobalt, palladium and platinum catalyst, but not the supported nickel catalyst, being used as catalyst. In all four cases no hydrogenation of the monoether to the diether worth mentioning was achieved.

COMPARISON EXAMPLES 5 AND 6

500 g of propylene glycol monobutyl ether from Example 1 and 25 g of Raney nickel, i.e. 5% by weight of nickel, relative to the 500 g of monobutyl ether, were initially introduced into a shaking autoclave. After flushing with nitrogen, the initially introduced mixture was heated to 220° C. with shaking and sufficient hydrogen was admitted so that an initial pressure of 9 MPa (Comparison Example 5) and 18 MPa (Comparison Example 6) was present. Even after a reaction time of 10 hours, no hydrogenation reaction could be detected in both cases.

We claim:

1. A process for the preparation of alkylene glycol dialkyl ethers from alkylene glycol monoalkyl ethers having a secondary hydroxyl group, which comprises reacting an alkylene glycol monoalkyl ether of the formula I $$R^1O(CH_2\underset{R^2}{CHO})_n-CH_2\underset{R^3}{CHOH}$$

in which $R^1$ is an alkyl radical having 1 to 25 carbon atoms, $R^2$ is H, $CH_3$ or $C_2H_5$ and, within the chain of the polyoxyalkylene radical, arranged randomly or in blocks, can also assume all three meanings, $R^3$ is $CH_3$ or $C_2H_5$ and n denotes 1 to 100, with hydrogen without pressure in the presence of nickel on a support as catalyst and recovering the alkylene glycol dialkyl ether formed from the reaction product.

2. The process as claimed in claim 1, wherein an alkylene glycol monoalkyl ether of the formula I is employed, in which $R^1$ is an alkyl radical having 4 to 18 carbon atoms, $R^2$ is H or $CH_3$ and, within the chain of the polyoxyalkylene radical, arranged randomly or in blocks, can also assume both meanings, $R^3$ is $CH_3$ and n is 5 to 50.

3. The process as claimed in claim 1, wherein a supported nickel catalyst containing 5 to 80% by weight of nickel on a support material is used, percent by weight being relative to the total catalyst, and sufficient supported nickel catalyst is employed that 0.5 to 15% by weight of nickel, relative to the amount of alkylene glycol monoalkyl ether to be reacted, are present.

4. The process as claimed in claim 1, wherein the hydrogen for hydrogenation is employed in an amount from 30 to 500 liters per kilogram of alkylene glycol monoalkyl ether per hour and the reaction is carried out at a temperature of 150° to 300° C.

5. The process as claimed in claim 1, wherein the alkylene glycol monoalkyl ether and such an amount of supported nickel catalyst, consisting of 30 to 65% by weight of nickel on a support material, percent by weight being relative to the total catalyst, are initially introduced into a reaction vessel equipped with a reflux condenser with water separator, that 1 to 10% by weight of nickel, relative to alkylene glycol monoalkyl ether, are present, the initially introduced mixture is heated to a temperature of 180° to 250° C., 50 to 250 liters of hydrogen per kilogram of alkylene glycol monoalkyl ether per hour are passed through the heated mixture until the reaction product has the desired low hydroxyl number, the excess of hydrogen being removed through the reflux condenser, and the alkylene glycol dialkyl ether formed is separated off from the catalyst employed.

* * * * *